(12) United States Patent
Feng

(10) Patent No.: US 8,784,374 B2
(45) Date of Patent: Jul. 22, 2014

(54) DISPOSABLE SELF-DESTRUCTIVE SYRINGE

(76) Inventor: Zhong Feng, Wuxi (CN)

( * ) Notice: Subject to any disclaimer, the term of this patent is extended or adjusted under 35 U.S.C. 154(b) by 1111 days.

(21) Appl. No.: 11/571,828

(22) PCT Filed: Apr. 5, 2006

(86) PCT No.: PCT/CN2006/000602
§ 371 (c)(1),
(2), (4) Date: Jan. 8, 2007

(87) PCT Pub. No.: WO2006/105729
PCT Pub. Date: Oct. 12, 2006

(65) Prior Publication Data
US 2009/0264823 A1    Oct. 22, 2009

(30) Foreign Application Priority Data
Apr. 5, 2005 (CN) .................. 2005 2 0011459 U

(51) Int. Cl.
*A61M 5/00* (2006.01)
*A61M 5/315* (2006.01)
(52) U.S. Cl.
USPC ........................................ 604/110; 604/220
(58) Field of Classification Search
USPC ......................................... 604/110, 218, 220
See application file for complete search history.

(56) References Cited

U.S. PATENT DOCUMENTS 4,995,869 A * 2/1991 McCarthy .................... 604/110
5,556,384 A   9/1996 da Encarnacao

FOREIGN PATENT DOCUMENTS

CN    02258578.8    10/2003
CN    03264428.0    8/2004

* cited by examiner

*Primary Examiner* — Nathan R Price
(74) *Attorney, Agent, or Firm* — Raymond Y. Chan; David and Raymond Patent Firm

(57) ABSTRACT

The present invention discloses a disposable self-destructive syringe, which belongs to syringes for medical treatment, comprises a needle (1), a tube (2), a injecting piston-rod (3), ratchet grooves (4), a restrictive step (5), an installation opening (6), an anti-return member (7), anti-return prods (8), ratchets (9), a sealing plug (10) and a reciprocal motion region (11). The needle is conglutinated on the tube, the injecting piston-rod is arranged in the tube, the anti-return member is arranged in the gap of the injecting piston-rod and in the rear end of the tube, and the sealing plug is arranged in the tube and mounted on the front end of the injecting piston-rod. The syringe is convenient to discharge the inhaled air as sucking medical liquid, begins to be self-destructive after sucking for predetermined amount and can not suck medical liquid again during and after injecting. Furthermore, the ratchet grooves arranged on the injecting piston-rod can be one or more, which the fewer the number of ratchet grooves, the larger the interval of discharging inhaled air will become. The disposable self-destructive syringe according to the invention of which dose is precise is convenient to operate and will be self-destructive once used.

20 Claims, 6 Drawing Sheets

DISPOSABLE SELF-DESTRUCTIVE SYRINGE

FIELD OF THE INVENTION

The present invention relates to a disposable self-destructive syringe which belongs to syringes for medical treatment.

BACKGROUND ART

Presently, the disposable sterile syringes widely used in hospitals and medical organizations domestically and abroad don't possess entirely the characteristic of being disposable in respect of their using performance due to their configuration, so they can be reused after some reset. For example, most of known self-destructive syringes are designed generally to destruct the sealing of injecting pistons after the medical liquid is fully expelled so that they can be used only once. However, if the injecting piston and injecting piston-rod are not advanced to the final position (i.e. some medical liquid is remained) when using the syringe, the piston can not be destructed and can be reused. In order to solve the above-mentioned problem, the China patent application with the application number CN03264428.0 filed on 18$^{th}$ Jun. 2003, the certificate is ZL03264428.0, the applicant is Wuxishiyushou medical-appliance Company and the designers are Fengzhong, Wangjunyi and Feijianguo disclosed a disposable self-destructive syringe comprising ratchet grooves and an anti-return member, wherein said teethed ratchet groove is provided in the entire gap in the injecting piston-rod and said anti-return member is arranged on the rear end of the ratchet grooves, and the ratchet grooves and the anti-return member are arranged together in the cylinder (i.e. the housing) of the syringe. When sucking medical liquid, the injecting piston-rod is pulled backward, but the anti-return prods provided on the anti-return member keeps still due to its pressing against the inwall of the cylinder, thereby the ratchet grooves pass the anti-return member. When stating injecting after sucking medical liquid, the anti-return member will be pushed forward together with the injecting piston-rod for being locked by the ratchet groove, and the piston-rod can not be pulled backward again to suck medical liquid because the anti-return member is continuously pressing against the inwall of the tube, thereby realizing the disposable function. But the said syringe has some clinical limitations. The syringe can not completely expel the air inhaled during sucking medical liquid and even may waste medical liquid for having no structure for expelling air. Furthermore, the syringe can not be used as high dose-precision syringe for injecting bacteria and insulin because of not having taken the remainder of medical liquid into account. In order to overcome the above limitations, the invention provides an improved disposable self-destructive syringe.

BRIEF DESCRIPTION OF THE INVENTION

An object of the invention is to provide a disposable self-destructive syringe which can easily discharge the inhaled air during sucking medical liquid and has very little remainder, and more specially, to provide a disposable self-destructive syringe which can perform air discharging action and can not be reused again after having sucked predetermined quantity of medical liquid and injected the same, so as to solve the problem of the prior art.

Another object of the invention is to provide a disposable self-destructive syringe which can easily discharge the inhaled air during sucking medical liquid, wherein the self-destructive function comes into effect immediately after predetermined quantity have being sucked, so that it is impossible to suck medical liquid again during and after injecting. Furthermore, the number of ratchet grooves can be set according to the requirements of the clinical applications, wherein the fewer the number of ratchet grooves, the wider the region for reciprocal motion will be and the larger the interval for expelling inhaled air will become.

The invention is realized by means of the following description to solve the above said problems:

A disposable self-destructive syringe comprises a cylinder on which a injecting needle is bonded; an injecting piston-rod arranged in the cylinder, an anti-return member arranged in the gap in the injecting piston-rod and positioned in the rear end of the cylinder; a sealing plug arranged in the cylinder and mounted on the front end of the injecting piston-rod; one or more ratchet grooves (4) are arranged on the front end of center gap in the injecting piston-rod; (3); a restrictive step (5) is arranged on the rear end of center gap of the injecting piston-rod, and an anti-return member (7) passes the restrictive step and comes into the cylinder; an installation opening (6) is provided on the latest end of center gap in the injecting piston-rod; a reciprocal motion region (11) is located on the center gap in the injecting piston-rod; the anti-return member is provided with ratchets (9), and the two sides of the anti-return member are provided with anti-return prods (8). In one embodiment, the anti-return member is made of spring steel sheet.

The present invention has following advantages as compared with the prior art disclosed by CN2631527:

One embodiment of the invention includes an additional reciprocal motion region (11), in which the injecting piston-rod can reciprocate to suck liquid and expel the inhaled air, which satisfies the clinical requirement;

2. The amount of remainder can be reduced because the needle (1) is bonded on the tube (2) directly, thereby satisfying the requirement of injecting bacteria and insulin. The syringe is convenient and reliable and can be self-destructive once being used.

LIST OF THE REFERENCE NUMBER 1 needle; 2 cylinder; 3 injecting piston-rod; 4 ratchet groove; 5 restrictive step; 6 installation opening; 7 anti-return member; 8 anti-return prod; 9 ratchet; 10 sealing plug; 11 reciprocal motion region

DETAILED DESCRIPTION OF THE INVENTION

The invention will be described in more detail with reference to the drawings and embodiments.

Figure 1:
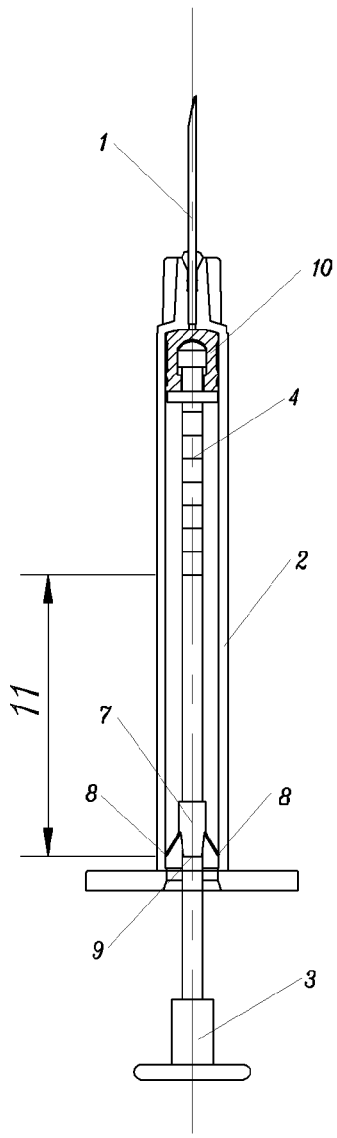
FIG. 1 shows the whole construction view of a disposable self-destructive syringe according to a first embodiment of the invention.
Figure 2:
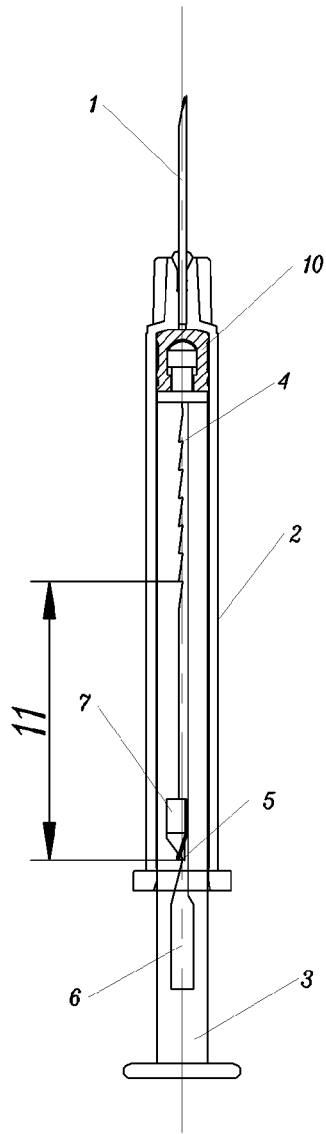
FIG. 2 is a left side construction view of the syringe in FIG. 1.

Referring to the drawings, the disposable self-destructive syringe according to the invention comprises a needle 1, a cylinder 2, an injecting piston-rod 3, an anti-return member 7 and a sealing plug 10, wherein the injecting piston-rod 3 is provided with ratchet grooves 4, a restrictive step 5, an installation opening 6 and a reciprocal motion region 11 (refer to FIGS. 1, 2 and 3, respectively), and the anti-return member 7 is provided with anti-return prods 8 and ratchets 9. In assembly, the anti-return member 7 enters into the restrictive step 5 through the installation opening 6 with the ratchets 9 being pressed against the restrictive step 5, and then the injecting piston-rod 3 is pushed into the bottom of the cylinder 2 together with the sealing plug 10 (as shown in FIGS. 1 and 2).

Figure 5:
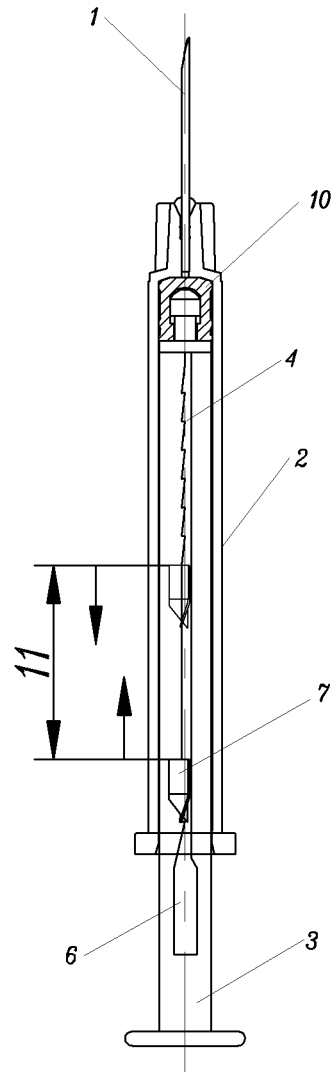
FIG. 5 is a schematic left side construction view of the syringe in FIG. 2, illustrating a region (11) in which a anti-return member (7) can reciprocate.
Figure 6:
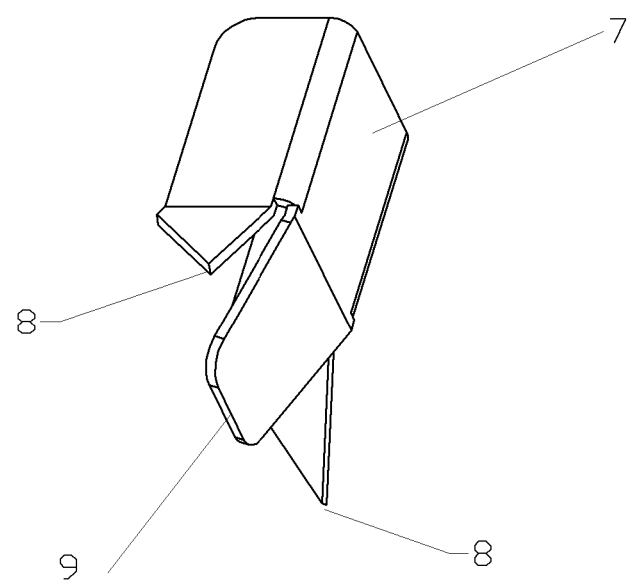
FIG. 6 is an enlarged perspective view of the anti-return member (7)
Figure 7A:
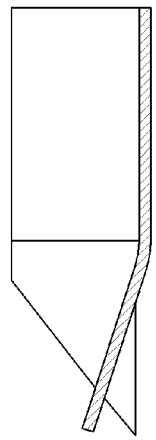
FIG. 7A is an enlarged, sectioned front view of the anti-return member (7)
Figure 7B:
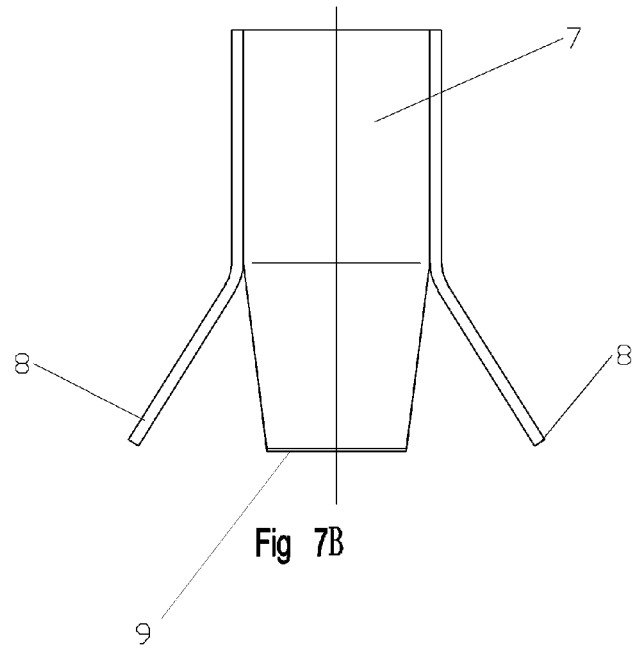
FIG. 7B is an enlarged vertical view of the anti-return member (7)
Figure 7C:
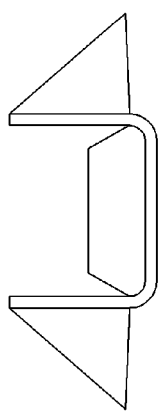
FIG. 7C is an enlarged side view of the anti-return member (7)

In operation, the injecting piston-rod 3 is pulled backward to suck some medical liquid. If air is inhaled before the anti-return member 7 entering into the ratchet grooves 4, the inhaled air can be expelled by means of the reciprocal motion region 11 (as shown in FIG. 5).

Figure 3:
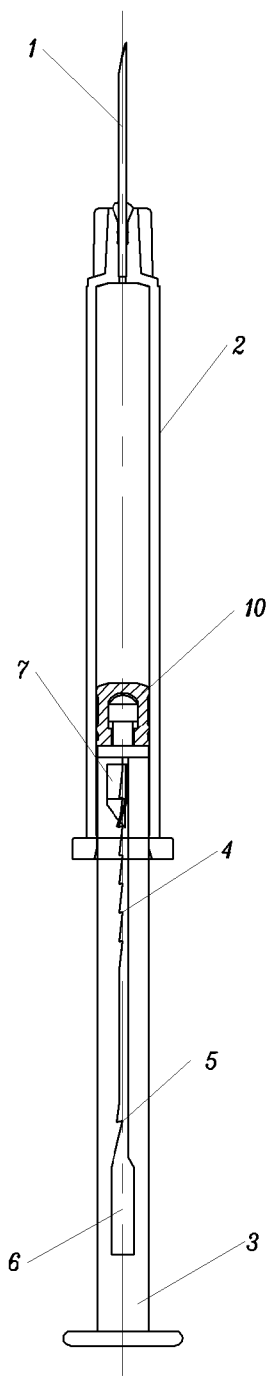
FIG. 3 is a left side construction view of the syringe in FIG. 2 with the cylinder being completely filled with the medical liquid.
Figure 4:
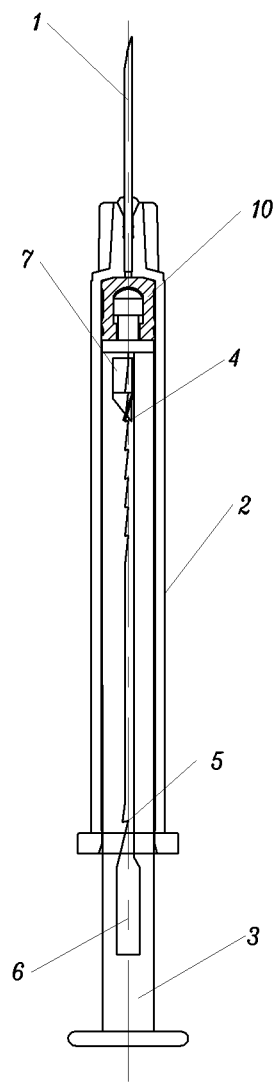
FIG. 4 is a left side construction view of the syringe in FIG. 2 when the injecting is completed.

When the inhaled air is discharged completely and the medical liquid is sucked once again, the ratchet grooves 4 pass the ratchets 9 (as shown in FIG. 3). In injection, the sealing plug 10, the injecting piston-rod 3 and the anti-return member 7 are pushed forward together and then the injecting piston-rod 3 can not be pulled backward, because otherwise the anti-return prods 8 will pierce into the inwall of the tube and the injection will end. As said above, now the injecting piston-rod 3 and the sealing plug 10 can never be pulled backward for the same reason relating to the anti-return prods 8.

Figure 8:
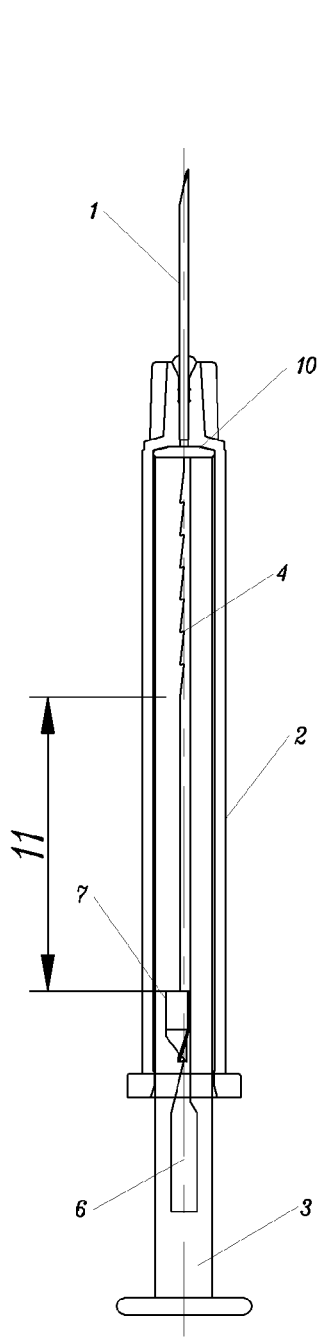
FIG. 8 shows the construction view of a disposable self-destructive syringe according to a second embodiment of the invention.
Figure 9:
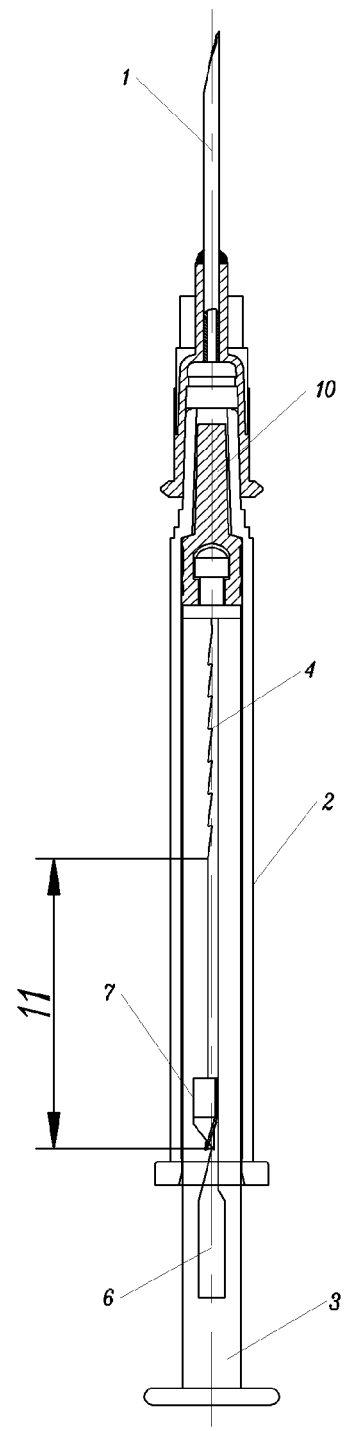
FIG. 9 shows the construction view of a disposable self-destructive syringe according to a third embodiment of the invention.

The other two embodiments (as shown in FIGS. 8 and 9) are of the same functioning principle. However, the needle is a separate member connected to the cylinder in FIG. 8, and the sealing plug and the injecting piston-rod are integrally formed by molding in FIG. 9.

The invention claimed is:

1. A disposable self-destructive syringe, comprising:
a cylinder, having a flat tubular inwall, bonding with an injecting needle;
a sealing plug disposed in said cylinder to slide along said inwall thereof in a sealed manner;
a one piece integrated injecting piston-rod having a front end coupling with said sealing plug to move said sealing plug within said cylinder, wherein said injecting piston-rod has a center gap defining a center ratchet groove at a front portion of said injecting piston-rod and a reciprocal motion region at a rear portion of said injecting piston-rod; and
an anti-return member slidably coupling with said injecting piston-rod in unidirectional manner, wherein when said injecting piston-rod is pulled backward for sucking liquid into said cylinder, said anti-return member is retained along said reciprocal motion region of said center gap for enabling said injecting piston-rod being reciprocally moved for expelling inhaled air out of said cylinder, wherein when said injecting piston-rod is pushed backward to move said anti-return member from said reciprocal motion region of said center gap to said ratchet groove, said anti-return member fixes at said injecting piston-rod along said ratchet groove, wherein when said injecting piston-rod is pushed forward during injection process, said injecting piston-rod and said anti-return member are moved at the same time, wherein said anti-return member pierces into said inwall of said cylinder, such that after said injection process is completed, said anti-return member is affixed in said cylinder to prevent said injecting piston-rod being pulled back in said cylinder.

2. The disposable self-destructive syringe, as recited in claim 1, wherein said injecting piston-rod further comprises a restrictive step formed at said center gap to define said reciprocal motion region between said ratchet groove and said restrictive step, such that when said anti-return member is moved across said restrictive step to said reciprocal motion region, said anti-return member is prohibited to move back to out of said reciprocal motion region.

3. The disposable self-destructive syringe, as recited in claim 1, wherein said injecting piston-rod further comprises one or more ratchets spacedly formed along said ratchet groove to engage with said anti-return member so as to fix said anti-return member at said ratchet groove.

4. The disposable self-destructive syringe, as recited in claim 2, wherein said injecting piston-rod further comprises one or more ratchets spacedly formed along said ratchet groove to engage with said anti-return member so as to fix said anti-return member at said ratchet groove.

5. The disposable self-destructive syringe, as recited in claim 1, wherein said anti-return member comprises two anti-return prods extending from two outer side of said anti-return member to pierce into said inwall of said cylinder in unidirectional manner.

6. The disposable self-destructive syringe, as recited in claim 4, wherein said anti-return member comprises two anti-return prods extending from two outer side of said anti-return member to pierce into said inwall of said cylinder in unidirectional manner.

7. The disposable self-destructive syringe, as recited in claim 5, wherein said anti-return member is made of spring steel sheet.

8. The disposable self-destructive syringe, as recited in claim 6, wherein said anti-return member is made of spring steel sheet.

9. The disposable self-destructive syringe, as recited in claim 2, wherein said injecting piston-rod further comprises an installation opening provided at a rear end of said center gap of said injecting piston-rod at a position behind said restrictive step, such that when said anti-return member passes said restrictive step from said installation opening to said reciprocal motion region, said anti-return member is prohibited to move back to out of said installation opening.

10. The disposable self-destructive syringe, as recited in claim 8, wherein said injecting piston-rod further comprises an installation opening provided at a rear end of said center gap of said injecting piston-rod at a position behind said restrictive step, such that when said anti-return member passes said restrictive step from said installation opening to said reciprocal motion region, said anti-return member is prohibited to move back to out of said installation opening.

11. A method of injecting liquid by a disposable self-destructive syringe which comprises a cylinder, having a flat tubular inwall, bonding with an injecting needle, a sealing plug disposed in said cylinder to slide along said inwall thereof in a sealed manner, an injecting piston-rod having a front end coupling with said sealing plug to move said sealing plug within said cylinder, and an anti-return member coupling with said injecting piston-rod, wherein the method comprises the steps of:

(a) pulling said injecting piston-rod backward for sucking liquid into said cylinder, wherein said injecting piston-rod has a center gap defining at least a center ratchet groove at a front portion of said injecting piston-rod and a reciprocal motion region at a rear portion of said injecting piston-rod;

(b) when said anti-return member is retained along said reciprocal motion region of said center gap of said injecting piston-rod, enabling said injecting piston-rod being reciprocally moved for expelling inhaled air out of said cylinder;

(c) pushing said injecting piston-rod backward to move said anti-return member from said reciprocal motion region of said center gap to said ratchet groove; and (d) pushing said injecting piston-rod and said anti-return member forward at the same time for discharging said liquid out of said cylinder via said sealing plug, wherein said anti-return member fixes at said injecting piston-rod along said ratchet groove and pierces into said inwall of said cylinder to prevent said injecting piston-rod being pulled back in said cylinder after said liquid is discharged, so as to self-destruct said disposable self-destructive syringe once being used.

12. The method as recited in claim 11 wherein, in the step (a), said anti-return member is retained along said reciprocal motion region when said injecting piston-rod is pulled backward.

13. The method, as recited in claim 11, wherein the step (c) further comprises a step of engaging said anti-return member with one or more ratchets spacedly formed along said ratchet groove to fix said anti-return member at said ratchet groove.

14. The method, as recited in claim 12, wherein the step (c) further comprises a step of engaging said anti-return member with one or more ratchets spacedly formed along said ratchet groove to fix said anti-return member at said ratchet groove.

15. The method, as recited in claim 11, wherein the step (b) further comprises a step of providing a restrictive step at said center gap to define said reciprocal motion region between said ratchet groove and said restrictive step, wherein when said anti-return member is moved across said restrictive step to said reciprocal motion region, said anti-return member is prohibited to move back to out of said reciprocal motion region.

16. The method, as recited in claim 14, wherein the step (b) further comprises a step of providing a restrictive step at said center gap to define said reciprocal motion region between said ratchet groove and said restrictive step, wherein when said anti-return member is moved across said restrictive step to said reciprocal motion region, said anti-return member is prohibited to move back to out of said reciprocal motion region.

17. The method, as recited in claim 11, wherein said anti-return member comprises two anti-return prods extending from two outer side of said anti-return member to pierce into said inwall of said cylinder in unidirectional manner.

18. The method, as recited in claim 16, wherein said anti-return member comprises two anti-return prods extending from two outer side of said anti-return member to pierce into said inwall of said cylinder in unidirectional manner.

19. The method, as recited in claim 16, before the step (a), further comprising a step of passing said anti-return member through said restrictive step from an installation opening to said reciprocal motion region, wherein said installation opening is provided at a rear end of said center gap of said injecting piston-rod at a position behind said restrictive step, such that when said anti-return member passes said restrictive step from said installation opening to said reciprocal motion region, said anti-return member is prohibited to move back to out of said installation opening.

20. The method, as recited in claim 18, before the step (a), further comprising a step of passing said anti-return member through said restrictive step from an installation opening to said reciprocal motion region, wherein said installation opening is provided at a rear end of said center gap of said injecting piston-rod at a position behind said restrictive step, such that when said anti-return member passes said restrictive step from said installation opening to said reciprocal motion region, said anti-return member is prohibited to move back to out of said installation opening.

* * * * *